United States Patent [19]

Eicken et al.

[11] Patent Number: 4,472,192
[45] Date of Patent: Sep. 18, 1984

[54] 5-AMINO-1-PHENYL-PYRAZOLE-4-CARBOXYLIC ACID DERIVATIVES AND THEIR USE FOR CONTROLLING UNDESIRABLE PLANT GROWTH

[75] Inventors: Karl Eicken, Wachenheim; Peter Plath, Ludwigshafen; Bruno Wuerzer, Otterstadt, all of Fed. Rep. of Germany

[73] Assignee: BASF Aktiengesellschaft, Fed. Rep. of Germany

[21] Appl. No.: 400,049

[22] Filed: Jul. 20, 1982

[30] Foreign Application Priority Data

Jul. 25, 1981 [DE] Fed. Rep. of Germany ....... 3129429

[51] Int. Cl.³ .................... C07D 231/14; A01N 43/56
[52] U.S. Cl. ...................................... 71/92; 548/362
[58] Field of Search ............................ 71/92; 548/362

[56] References Cited

U.S. PATENT DOCUMENTS 3,567,735 3/1971 Druey et al. .................... 260/310

FOREIGN PATENT DOCUMENTS 26034 4/1981 European Pat. Off. ............ 548/362
34945 9/1981 European Pat. Off. .

OTHER PUBLICATIONS

Arch. Pharm., vol. 312 (1979), pp. 703-707.

*Primary Examiner*—Henry R. Jiles
*Assistant Examiner*—Kurt G. Briscoe
*Attorney, Agent, or Firm*—Keil & Weinkauf

[57] ABSTRACT

5-Amino-1-phenyl-pyrazole-4-carboxylic acid derivatives of the formula

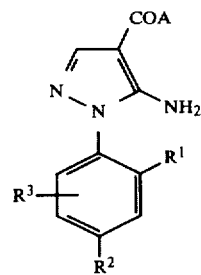

where $R^1$, $R^2$, $R^3$ and A have the meanings given in the description, are used for controlling undesirable plant growth.

6 Claims, No Drawings

5-AMINO-1-PHENYL-PYRAZOLE-4-CARBOXYLIC ACID DERIVATIVES AND THEIR USE FOR CONTROLLING UNDESIRABLE PLANT GROWTH

The present invention relates to 5-amino-1-phenyl-pyrazole-4-carboxylic acid derivatives and their salts, herbicides containing these compounds as the active ingredients, and methods of controlling undesirable plant growth using the compounds.

5-Amino-1-phenyl-pyrazole-4-carboxylic acid esters in which the phenyl ring is substituted by chlorine have been disclosed (U.S. Pat. No. 3,567,735; Arch. Pharm. 312 (1979), 703). They are intermediates for the synthesis of diuretics or of antibacterial compounds, but nothing has been disclosed relating to herbicidal properties of these compounds.

We have found that 5-amino-1-phenyl-pyrazole-4-carboxylic acid derivatives of the formula

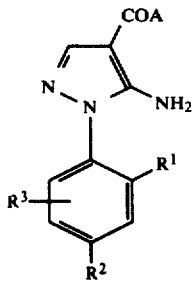

wherein $R^1$ is methyl, trifluoromethyl, chlorine or bromine, $R^2$ is chlorine, bromine, iodine or methylsulfonyl, $R^3$ is a methoxy radical in the 5-position or is hydrogen, chlorine or bromine, and A is $-OR^4$, $-NR^5R^6$ or $-ON=CR^5R^6$, where $R^4$ is alkenyl of 3 to 12 carbon atoms which is unsubstituted or substituted by phenyl, or is alkynyl of 3 to 10 carbon atoms, phenalkyl, where alkyl is of 1 to 8 carbon atoms, phenoxyalkyl, where alkyl is of 2 to 8 carbon atoms and the phenyl ring is unsubstituted or substituted by halogen, alkyl of 1 to 4 carbon atoms or methoxy, cycloalkylmethyl of 4 to 7 carbon atoms in total, or alkyl of 2 to 4 carbon atoms which is substituted by alkoxy of 1 to 12 carbon atoms, alkylthio of 1 to 12 carbon atoms, allyloxy, propargyloxy, chlorine or bromine, and $R^5$ and $R^6$ are identical or different and each is alkyl of 1 to 6 carbon atoms, or $R^5$ and $R^6$ together are alkylene of 4 to 6 carbon atoms, and salts of the compounds of the formula I have a surprisingly powerful and at the same time selective herbicidal action.

5-Amino-1-phenyl-pyrazole-4-carboxylic acid derivatives of the formula I are obtained by reacting a substituted phenylhydrazine of the formula

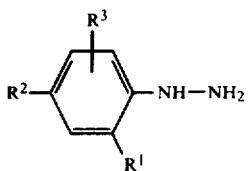

where $R^1$, $R^2$ and $R^3$ have the above meanings, or a mineral acid salt of a phenylhydrazine, with a substituted 2-cyanoacrylic acid derivative of the formula

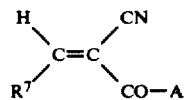

where $R^7$ is alkoxy of 1 to 4 carbon atoms, dialkylamino, where each alkyl is of 1 to 4 carbon atoms, or hydroxyl, and A is $-OR^4$ or $-NR^5R^6$, where $R^4$, $R^5$ and $R^6$ have the above meanings, in the presence or absence of an acid acceptor at below 70° C. to give a substituted 2'-phenyl-hydrazino-2-cyanoacrylic acid derivative of the formula

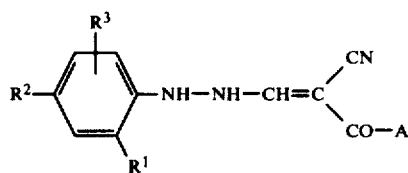

where $R^1$, $R^2$, $R^3$ and A have the above meanings, and cyclizing the product by heating it to above 70° C. (process A) or by treating it with aqueous mineral acid at from 0° to 150° C., preferably at from 20° to 100° C. (process B).

Particularly suitable solvents for process A are alcohols, eg. methanol and ethanol, but ethers, eg. dioxane, tetrahydrofuran and anisole, or hydrocarbons, eg. toluene and xylene, can also be used. When the reaction between the compounds of the formulae II and III has ended, or after the cyclization, the particular solution is cooled and the product formed is isolated by filtration and if necessary purified by recrystallization. If the cyclization is carried out by process B using aqueous mineral acid, preferably 5-38% strength (% by weight) hydrochloric acid or 5-50% strength sulfuric acid, the reaction mixture is diluted with 2-20 times the volume of water when the reaction has ended, and the cyclization product is filtered off with suction, washed neutral, with addition of dilute alkali or ammonia, and if necessary recrystallized.

5-Amino-1-phenyl-pyrazole-4-carboxylic acid derivatives of the formula I are also obtained in a single stage by reacting a substituted phenylhydrazine of the formula II with a substituted 2-cyanoacrylic acid derivative of the formula III at about 70° C. (process C). Suitable solvents are those mentioned for process A, preferably alcohols, having boiling points above 70° C. The end products are isolated as described for process A. Not less than the molar amount, based on the substituted phenylhydrazine of the formula II, and preferably the stoichiometric amount of the 2-cyanoacrylic acid derivative of the formula III is used. If, instead of a free phenylhydrazine of the formula II, a mineral acid salt thereof, eg. the hydrochloride or sulfate, is used in process A or C, it is advantageous first to liberate the substituted phenylhydrazine of the formula II with an equivalent amount of an alkali metal alcoholate or sodium acetate and then to carry out the reaction.

5-Amino-1-phenyl-pyrazole-4-carboxylic acid derivative of the formula I where A is $-OR^4$ or $-ON=CR^5R^6$, where $R^4$, $R^5$ and $R^6$ have the above meanings, are also obtained by reacting a 5-amino-1-phenyl-pyrazole-4-carboxylic acid alkyl ester of the formula

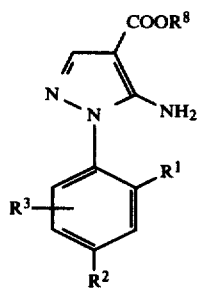

where $R^1$, $R^2$ and $R^3$ have the above meanings and $R^8$ is alkyl of 1 to 3 carbon atoms, with an alcohol of the formula $R^4OH$ or an oxime of the formula $HO-N=CR^5R^6$, where $R^4$, $R^5$ and $R^6$ have the above meanings, in the presence of an alcoholate as a catalyst.

This reaction is carried out above the boiling point of the alcohol component of the ester employed, ie. at from 80° to 250° C. The alcohol of the formula $R^4OH$ or the oxime of the formula $HO-N=CR^5R^6$ is advantageously employed in an excess of from 10 to 1,000 moles per mole of starting compound of the formula V. Suitable catalysts include alkali metal alcoholates, especially alkali metal methylates, these being added in amounts of from 1 to 20 mole percent, based on the ester of the formula V used. To isolate the end product, the excess alcohol of the formula $R^4OH$ or oxime of the formula $HO-N=CR^5R^6$ is removed by evaporation or, if it is water-soluble, by dilution with water. If necessary, the 5-amino-1-phenyl-pyrazole-4-carboxylic acid derivative of the formula I can be isolated by precipitation as the mineral acid salt, or can be further purified by crystallization.

Suitable acids which form salts with the 5-amino-1-phenyl-pyrazole-4-carboxylic acid derivatives of the formula I include strong inorganic acids, in particular mineral acids, and strong organic acids, eg. trifluoroacetic acid, sulfuric acid, hydrochloric acid, hydrobromic acid and benzenesulfonic acid.

Those phenylhydrazines of the formula II which are not already known can be prepared in a conventional manner (Houben-Weyl, Methoden der organischen Chemie, Volume 10/2, page 280 et seq., Georg-Thieme-Verlag, Stuttgart, 1967). The 2-cyanoacrylic acid esters of the formula III are known in some cases, or they can be prepared in a conventional manner (German Laid-Open Application DOS No. 2,635,841; Chem. Ber. (1964) 97, 3397).

If A in formula I is $-OR^4$, $R^4$ is, for example, straight-chain or branched alkenyl of 3 to 12 carbon atoms, preferably of 3 to 6 carbon atoms, which is unsubstituted or substituted by phenyl, eg. allyl, crotonyl, methallyl, 3-methyl-but-2-enyl, 3-methyl-but-3-enyl, hex-5-enyl, undec-10-enyl, 2-phenyl-prop-2-enyl or 3-phenyl-prop-2-enyl, or is straight-chain or branched alkynyl of 3 to 10 carbon atoms, in particular of 3 to 6 carbon atoms, eg. propargyl, but-2-ynyl, or hex-5-ynyl, or is phenalkyl, where alkyl is of 1 to 8 carbon atoms, preferably of 1 to 3 carbon atoms, eg. benzyl, 2-phenethyl, 2-phenyl-n-propyl or 3-phenyl-n-propyl, or is phenoxyalkyl, where alkyl is of 2 to 8 carbon atoms, preferably of 2 to 4 carbon atoms, and the phenyl ring is unsubstituted or substituted by halogen, alkyl of 1 to 4 carbon atoms or methoxy, eg. 2-phenoxyethyl, 3-phenoxy-n-propyl, 2-phenoxy-n-propyl or 4-phenoxy-n-butyl, or is cycloalkylmethyl of 4 to 7 carbon atoms in total, eg. cyclopropylmethyl, cyclopentylmethyl or cyclohexylmethyl, or is alkyl of 2 to 4 carbon atoms which is substituted by alkoxy of 1 to 12 carbon atoms, preferably of 1 to 6 carbon atoms, alkylthio of 1 to 12 carbon atoms, preferably of 1 to 6 carbon atoms, allyloxy, propargyloxy, chlorine or bromine, eg. 2-methoxy-ethyl, 2-ethoxy-ethyl, 2-(n-propoxy)-ethyl, 2-(n-butoxy)-ethyl, 2-(n-hexoxy)-ethyl, 3-methoxy-n-propyl, 2-methoxy-n-propyl, 2-chloroethyl, 2-bromoethyl, 3-chloro-n-propyl, 4-chloro-n-butyl, 2-methylthioethyl, 2-(n-propylthio)-ethyl, 2-(n-butylthio)-ethyl, 4-methoxy-n-butyl or 3-methoxy-n-butyl.

If A in formula I is $-NR^5R^6$ or $-O-C=NR^5R^6$, $R^5$ and $R^6$ are, for example, alkyl of 1 to 6 carbon atoms, preferably of 1 to 4 carbon atoms, or $R^5$ and $R^6$ together are alkylene of 4 to 6 carbon atoms. Suitable amino radicals of the formula $-NR^5R^6$ thus include dimethylamino, diethylamino, di-n-propyl-amino, di-n-butylamino, methylethylamino, pyrrolidino and piperidino. The oxime ethers of the formula I are based on, for example, acetone oxime, methyl ethyl ketone oxime, diethyl ketone oxime, cyclopentenone oxime or cyclohexanone oxime.

Preferred compounds are those where A is $-OR^4$, where $R^4$ is straight-chain or branched alkenyl of 3 to 12 carbon atoms, or alkyl of 2 to 4 carbon atoms which is substituted by alkoxy of 1 to 12 carbon atoms, preferably of 1 to 6 carbon atoms.

In the Examples which follow and which illustrate the preparation of the intermediates of the formulae IV and V and of the end products of the formula I, parts by weight bear the same relation to parts by volume as that of the kilogram to the liter.

EXAMPLE A 148.1 parts by weight of 2,4,6-trichlorophenyl-hydrazine were added to a solution of 108.5 parts by weight of methyl ethoxymethylene-2-cyanoacetate in 1,000 parts by volume of methanol. A crystal sludge precipitated out of the solution and was stirred for 3 hours, and the precipitate was filtered off with suction and dried under reduced pressure at 40° C. to give 187.4 parts by weight of methyl 2'-(2,4,6-trichlorophenyl)-hydrazino-2-cyanoacrylate of melting point 174°-175° C.

$C_{11}H_8Cl_3N_3O_2$ (molecular weight 320.5)

calculated: C: 41.22; H: 2.52; N: 13.11; found: C: 40.9; H: 2.8; N: 12.8.

EXAMPLE B

A suspension of 21.4 parts by weight of 2,4-dichlorophenylhydrazine hydrochloride in 150 parts by volume of methanol was neutralized by addition of about 18 parts by weight of 30% strength sodium ethylate solution, 15.5 parts by weight of methyl ethoxymethylene-2-cyanoacetate were added and the mixture was stirred at 25° C. for 3 hours and then refluxed for 15 minutes. The methanol was evaporated off from the filtrate under reduced pressure, and the residue was recrystallized from ethanol at 50° C. to give 17.5 parts by weight of methyl 2'-(2,4-dichlorophenyl)-hydrazino-2-cyanoacrylate of melting point 154°-156° C.

$C_{11}H_9Cl_2N_3O_2$ (molecular weight 286)

calculated: C: 46.18; H: 3.17; N: 14.69; found: C: 46.0 H: 3.2; N: 14.8.

The following 2'-phenylhydrazino-2-cyanoacrylic acid esters of the formula

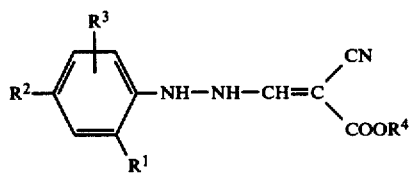  (IV)

were prepared in a similar manner:

| $R^1$ | $R^2$ | $R^3$ | $R^4$ | Melting point [°C.] |
|---|---|---|---|---|
| Cl | Cl | H | $C_2H_5$ | 175 |
| Cl | Cl | 6-Cl | $C_2H_5$ | 166 |
| Cl | Cl | 6-Cl | i-$C_3H_7$ | 130 |
| $CH_3$ | Cl | H | $CH_3$ | 140 |
| Br | Br | 6-Br | $CH_3$ | 182 |
| Cl | Cl | 5-Cl | $CH_3$ | 195 |

The following 2'-phenylhydrazino-2-cyanoacrylic acid esters can be prepared in a similar manner:

| $R^1$ | $R^2$ | $R^3$ | $R^4$ | Melting point [°C.] |
|---|---|---|---|---|
| Cl | Br | 5-Cl | $CH_3$ | |
| $CH_3$ | Br | H | $CH_3$ | |
| $CH_3$ | Br | 6-Br | $CH_3$ | |
| $CH_3$ | Cl | 6-Cl | $CH_3$ | |
| Cl | Cl | 6-Br | $CH_3$ | |
| Cl | Br | 6-Br | $CH_3$ | |
| Cl | Br | 6-Cl | $CH_3$ | |
| Br | Cl | 6-Br | $CH_3$ | |
| Br | Br | H | $CH_3$ | |
| Cl | Cl | 5-$CH_3O$ | $CH_3$ | |

EXAMPLE C 90.0 parts by weight of methyl 2'-(2,4,6-trichlorophenyl)-hydrazino-2-cyanoacrylate were stirred in 300 parts by volume of 18% strength hydrochloric acid at 80° C. for 5 hours. The mixture was cooled and diluted with 500 parts by volume of water, and the precipitate was filtered off with suction and washed neutral with water and sodium bicarbonate solution to give 70.6 parts by weight of methyl 5-amino-1-(2,4,6-trichlorophenyl)-pyrazole-4-carboxylate of melting point 179°–180° C.

$C_{11}H_8Cl_3N_3O_2$ (molecular weight 320.5)

calculated: C: 41.22; H: 2.52; N: 13.11; found: C: 41.4; H: 2.8; N: 12.6

EXAMPLE D 15.0 parts by weight of methyl 2'-(2,4,6-dichlorophenyl)-hydrazino-2-cyanoacrylate were stirred in 50 parts by volume of concentrated hydrochloric acid at 25° C. for 12 hours, and the mixture was then stirred into 500 parts by volume of ice-water. The resulting precipitate was filtered off with suction and washed neutral with water and sodium bicarbonate solution to give 14.2 parts by weight of methyl 5-amino-1-(2,4-dichlorophenyl)-pyrazole-4-carboxylate of melting point 143°–145° C.

$C_{11}H_9Cl_2N_3O_2$ (molecular weight 286)

calculated: C: 46.18; H: 3.17; N: 14.69; found: C: 46.2; H: 3.2; N: 14.7.

EXAMPLE E 45.0 parts by weight of methyl 2'-(2,4-dichlorophenyl)-hydrazino-2-cyanoacrylate in 200 parts by volume of n-propanol were refluxed for 6 hours. The mixture was cooled, and the precipitate was filtered off with suction to give 34.6 parts by weight of methyl 5-amino-1-(2,4-dichlorophenyl)-pyrazole-4-carboxylate of melting point 144°–145° C.

EXAMPLE F 21.2 parts by weight of 2,4,6-trichlorophenylhydrazine and 15.5 parts by weight of methyl ethoxymethylene-2-cyanoacrylate in 120 parts by volume of n-butanol were refluxed for 2 hours. The mixture was cooled, and the precipitate was filtered off with suction to give 22.8 parts by weight of methyl 5-amino-1-(2,4,6-trichlorophenyl)-pyrazole-4-carboxylate of melting point 180°14 181° C.

The following 5-amino-1-phenyl-pyrazole-4-carboxylic acid esters of the formula V

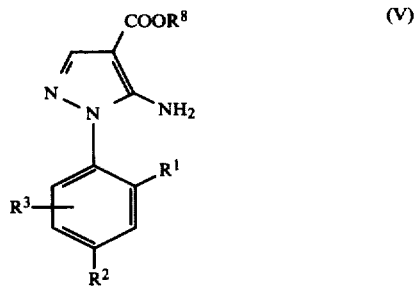  (V)

were obtained in a similar manner.

| $R^1$ | $R^2$ | $R^3$ | $R^8$ | Melting point [°C.] |
|---|---|---|---|---|
| Cl | Cl | H | $C_2H_5$ | 109 |
| Cl | Cl | 6-Cl | $C_2H_5$ | 105 |
| Cl | Cl | 6-Cl | i-$C_3H_7$ | 152 |
| $CH_3$ | Cl | H | $CH_3$ | 109 |
| Br | Br | 6-Br | $CH_3$ | 194 |
| Cl | Br | 5-Cl | $CH_3$ | 173 |
| Cl | Cl | 5-Cl | $CH_3$ | 175 |
| $CH_3$ | Br | H | $CH_3$ | 123 |
| $CH_3$ | Br | 6-Br | $CH_3$ | 175 |
| Cl | Cl | 6-Br | $CH_3$ | 199 |
| Cl | Br | 6-Br | $CH_3$ | 208 |
| Cl | Br | 6-Cl | $CH_3$ | 181 |
| Br | Cl | 6-Br | $CH_3$ | 172 |
| Cl | Cl | 5-$CH_3O$ | $CH_3$ | 182 |
| Cl | I | H | $CH_3$ | 180 |
| Cl | H | 3-Cl | $CH_3$ | 164 |
| Cl | Cl | 6-Cl | n-$C_3H_7$ | 92 |
| $CF_3$ | Cl | H | $CH_3$ | 146 |
| Cl | $SO_2CH_3$ | H | $CH_3$ | 215 |

The following 5-amino-1-phenyl-pyrazole-4-carboxylic acid esters of the formula V can be obtained in a similar manner:

| $R^1$ | $R^2$ | $R^3$ | $R^8$ | Melting point [°C.] |
|---|---|---|---|---|
| $CH_3$ | Cl | 6-Cl | $CH_3$ | |
| Br | Br | H | $CH_3$ | |
| Cl | Br | 6-Cl | $CH_3$ | |

EXAMPLE 1

20.5 parts by weight of 2,6-dichloro-4-bromophenylhydrazine and 14.5 parts by weight of allyl ethoxymethylene-2-cyanoacetate in 100 parts by volume of n-butanol were refluxed for 4 hours. The butanol was evaporated off, the oily residue was dissolved in 150 parts by volume of ether, and dry halogen chloride gas was passed in, with ice-cooling. The hydrochloride which had precipitated was stirred with saturated sodium bicarbonate solution, and the precipitate was filtered off with suction and dried under reduced pressure to give 24.8 parts by weight of allyl 5-amino-1-(2,6-dichloro-4-bromophenyl)-pyrazole-4-carboxylate of melting point 85° C. (active ingredient No.6).

$C_{13}H_{10}N_3O_2Cl_2Br$ (molecular weight 391)

calculated: C: 39.8; H: 2.55; N: 10.77; found: C: 39.2; H: 2.7; N: 10.4.

EXAMPLE 2

12.7 parts by weight of 2,4,6-trichlorophenylhydrazine and 10.8 parts by weight of p-dimethylamino-α-cyanoacrylic acid N,N,-dimethylamide in 100 parts by volume of n-butanol were refluxed for 12 hours. The butanol was evaporated off, and the crystalline residue was moistened with ether to give 9.4 parts by weight of 5-amino-1-(2,4,6-trichlorophenyl)-pyrazole-4-carboxylic acid N,N-dimethylamide of melting point 226°-228° C. (active ingredient No.16).

$C_{12}H_{11}N_4Cl_3O$ (molecular weight 333.5)

calculated: C: 43.20; H: 3.32; N: 16.79; found: C: 43.6; H: 3.2; N: 16.8

EXAMPLE 3

12.0 parts by weight of methyl 5-amino-1-(2,4,6-trichlorophenyl)-pyrazole-4-carboxylate, 24.0 parts by weight of 3-methylbut-2-enol and 0.5 parts by weight of sodium methylate were refluxed for 2 hours (complete conversion), while dry nitrogen was passed over. The excess alcohol was removed under a reduced pressure of from 0.5 to 1.0 mbar/50° C., and the residue was dissolved in 100 ml of ether and precipitated with dry hydrogen chloride gas. The hydrochloride was filtered off with suction and stirred with saturated sodium bicarbonate solution, and the precipitate was filtered off with suction and dried under reduced pressure at 50° C. to give 10.6 g of 3-methylbut-2-enyl 5-amino-1-(2,4,6-trichlorophenyl)-pyrazole-4-carboxylate of melting point 102°-105° C. (active ingredient No.10).

$C_{15}H_{14}N_3O_2Cl_2$ (molecular weight 374.5)

calculated: C: 48.09; H: 3.77; N: 11.22; found: C: 48.3; H: 4.0; N: 11.1;

EXAMPLE 4

10.0 parts by weight of methyl 5-amino-1-(2,4,6-trichlorophenyl)-pyrazole-4-carboxylate, 22.5 parts by weight of acetone oxime and 0.5 part by weight of sodium methylate were stirred at 100° C. for 8 hours (50% conversion), while dry nitrogen was passed over. The mixture was cooled, the crude product was partitioned between 150 parts by volume of ether and 100 parts by volume of water, and the organic phase was washed with three times 100 parts by volume of water, dried under reduced pressure and concentrated. Chromatography of the residue on silica gel (80 g) with a 3/7 mixture of ethyl acetate and toluene gave 2.2 parts by weight of 5-amino-1-(2,4,6-trichlorophenyl)-pyrazole-4-carboxylic acid acetone oxime ester (active ingredient No.20) of melting point 194°-196° C. (from toluene).

$C_{13}H_{11}N_4O_2Cl_3$ (molecular weight 362)

calculated: C: 43.18; H: 3.07; N: 15.49; found: C: 43.3; H: 3.1; N: 15.2.

The following 5-amino-1-phenyl-pyrazole-4-carboxylic acid derivatives of the formula I and their salts have been prepared by one of the processes described above:

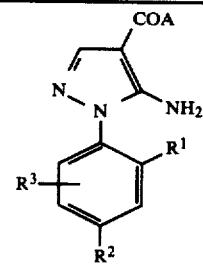

| No. | $R^1$ | $R^2$ | $R^3$ | A | M.p. [°C.] |
|---|---|---|---|---|---|
| 1 | $CH_3$ | Cl | H | $OCH_2CH=CH_2$ | oil |
| 2 | Cl | Cl | H | $OCH_2CH=CH_2$ | 88–90 |
| 3 | Cl | Cl | 6-Cl | $OCH_2CH=CH_2$ | 118–120 |
| 4 | Cl | $SO_2CH_3$ | H | $OCH_2CH=CH_2$ | 153 |
| 5 | Cl | Cl | 6-Br | $OCH_2CH=CH_2$ | 135 |
| 6 | Cl | Br | 6-Cl | $OCH_2CH=CH_2$ | 85 |
| 7 | Br | Br | 6-Br | $OCH_2CH=CH_2$ | 148 |
| 8 | Cl | Cl | 6-Cl | $OCH_2-C_6H_5$ | 157 |
| 9 | Cl | Cl | 6-Cl | $OCH_2C(CH_3)=CH_2$ | 110 |
| 10 | Cl | Cl | 6-Cl | $OCH_2CH=C(CH_3)_2$ | 102–105 |
| 11 | Cl | Cl | 6-Cl | $O(CH_2)_2OCH_3$ | 140–142 |
| 12 | Cl | Cl | 6-Cl | $O(CH_2)_4CH=CH_2$ | oil |
| 13 | Cl | Cl | 6-Cl | $O(CH_2)_9CH=CH_2$ | oil |
| 14 | Cl | Cl | 6-Cl | $O(CH_2)_2C_6H_5$ | 142–144 |
| 15 | Cl | Cl | 6-Cl | $OCH_2CH=CH_2.HCl$ | 158–160 |
| 16 | Cl | Cl | 6-Cl | $N(CH_3)_2$ | 226–228 |
| 17 | Cl | Cl | 6-Cl | $O(CH_2)_3C_6H_5$ | 112 |
| 18 | Cl | Cl | 6-Cl | $OCH_2CH(CH_3)C_6H_5$ | 60–65 |
| 19 | Cl | Cl | 6-Cl | $O(CH_2)_2OC_6H_5$ | 164–166 |
| 20 | Cl | Cl | 6-Cl | $ON=C(CH_3)_2$ | 194–196 |

The compounds of the formula I may be converted into conventional formulations, such as solutions, powders, suspensions (including high-percentage aqueous, oily or other suspensions), dispersions, emulsions, oil dispersions, pastes, dusts, broadcasting agents, or granules. The forms of application depend entirely on the purpose for which the agents are being used, but they must ensure as fine a distribution of the active ingredient as possible.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The herbicidal agents generally contain from 0.1 to 95, and preferably 0.5 to 90, % by weight of active ingredient.

The application rates depend on the composition and growth stages of the weed flora, and range from 0.1 to 15 kg/ha and more, preferably from 0.1 to 4 kg/ha; the higher application rates are to be used where total plant destruction is desired.

Application may be effected pre- or postemergence.

The agents, or the ready-to-use formulations prepared therefrom, such as solutions, emulsions, suspensions, powders, dusts, pastes or granules, are applied in conventional manner, e.g., by spraying, atomizing, dusting, scattering, treating seed, or watering.

If certain crop plants tolerate, on leaf application, the active ingredients less well, application techniques may be used in which the herbicidal agents are sprayed from suitable equipment in such a manner that the leaves of sensitive crop plants are if possible not touched, and the agents reach the soil or the unwanted plants growing beneath the crop plants (post-directed, lay-by treatment).

Examples of formulations are given below.

I. 90 parts by weight of compound 17 is mixed with 10 parts by weight of N-methyl-alpha-pyrrolidone. A mixture is obtained which is suitable for application in the form of very fine drops.

II. 10 parts by weight of compound 12 is dissolved in a mixture consisting of 90 parts by weight of xylene, 6 parts by weight of the adduct of 8 to 10 moles of ethylene oxide and 1 mole of oleic acid-N-monoethanolamide, 2 parts by weight of the calcium salt of dodecylbenzenesulfonic acid, and 2 parts by weight of the adduct of 40 moles of ethylene oxide and 1 mole of castor oil.

III. 20 parts by weight of compound 8 is dissolved in a mixture consisting of 60 parts by weight of cyclohexanone, 30 parts by weight of isobutanol, 5 parts by weight of the adduct of 7 moles of ethylene oxide and 1 mole of isooctylphenol, and 5 parts by weight of the adduct of 40 moles of ethylene oxide and 1 mole of castor oil.

IV. 20 parts by weight of compound 13 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide and 1 mole of castor oil.

V. 80 parts by weight of compound 20 is well mixed with 3 parts by weight of the sodium salt of diisobutylnaphthalene-alpha-sulfonic acid, 10 parts by weight of the sodium salt of a lignin-sulfonic acid obtained from a sulfite waste liquor, and 7 parts by weight of powdered silica gel, and triturated in a hammer mill.

VI. 5 parts by weight of compound 19 is intimately mixed with 95 parts by weight of particulate kaolin. A dust is obtained containing 5% by weight of the active ingredient.

VII. 30 parts by weight of compound 3 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound 2 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04 wt% of active ingredient.

IX. 20 parts of compound 4 is intimately mixed with 12 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The herbicidal action of 5-amino-1-phenylpyrazole-4-carboxylates of the formula I on the growth of crop and unwanted plants is demonstrated in greenhouse experiments.

The vessels employed were plastic flowerpots having a volume of 300 cm$^3$, and which were filled with a sandy loam containing about 1.5% humus. In the case of Galium aparine, peat was liberally added to ensure better emergence and growth. The seeds of the test plants were sown shallow, and separately, according to species.

For the postemergence treatment, the plants were first grown in the vessels to a height of from 3 to 10 cm, depending on growth form, before being treated. For this treatment, either plants which had been sown directly in the pots and grown there were selected, or plants which had been grown separately as seedlings and transplanted to the experiment vessels a few days before treatment. The application rates varied from active ingredient to active ingredient.

The pots were set up in the greenhouse—species from warmer areas at from 20° to 35° C., and species from moderate climates at 15° to 25° C. The experiments were run for from 2 to 3 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The plants used in the experiments were *Abutilon theoprasti, Amaranthus* spp., *Avena sativa, Chenopodium album, Galeopsis* spp., *Galium aparine, Hordeum vulgare, Ipomoea* spp., *Malva neglecta, Solanum nigrum, Triticum aestivum, Veronica persica,* and *Viola tricolor.*

In these experiments, compounds nos. 3, 12, 13 and 17, applied postemergence, had a good action on a number of broadleaved unwanted plants. Cereal species such as barley and wheat remained substantially unaffected, or were only slightly and temporarily damaged. Compound no. 8, applied postemergence, had an action on the broadleaved weeds *Galeopsis* spp., *Amaranthus* spp. and *Solanum nigrum.*

In view of the many application methods possible, the herbicides according to the invention can be used in a further, large number of crops for removing unwanted plant growth.

The following crops may be mentioned by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rape |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |

-continued

| Botanical name | Common name |
| --- | --- |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the novel 5-amino-1-phenyl-pyrazole-4-carboxylates may be mixed and applied together with numerous representatives of other herbicidal or growth-regulating active ingredient groups. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the novel compounds, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may be also added.

We claim:

1. A 5-Amino-1-phenyl-pyrazole-4-carboxylic acid derivative of the formula

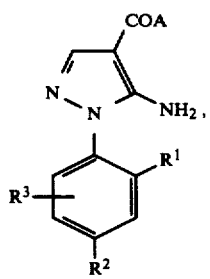 (I)

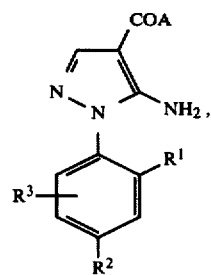 (I)

where $R^1$ is methyl, trifluoromethyl, chlorine or bromine, $R^2$ is chlorine, bromine, iodine or methylsulfonyl, $R^3$ is a methoxy radical in the 5-position or is hydrogen, chlorine or bromine, and A is $-OR^4$, where $R^4$ is alkenyl of 3 to 12 carbon atoms which is unsubstituted or substituted by phenyl, or is alkynyl of 3 to 10 carbon atoms, phenalkyl, where alkyl is of 1 to 8 carbon atoms, phenoxyalkyl, where alkyl is of 2 to 8 carbon atoms and the phenyl ring is unsubstituted or substituted by halogen, alkyl of 1 to 4 carbon atoms or methoxy, cycloalkylmethyl of 4 to 7 carbon atoms in total, or alkyl of 2 to 4 carbon atoms which is substituted by alkoxy of 1 to 12 carbon atoms, alkylthio of 1 to 12 carbon atoms, allyloxy, propargyloxy, chlorine or bromine, and salts thereof.

2. A 5-Amino-1-phenyl-pyrazole-4-carboxylic acid derivative of the formula I as claimed in claim 1, wherein A is $-OR^4$, $R^4$ denoting alkenyl of 3 to 12 carbon atoms or alkyl of 2 to 4 carbon atoms which is substituted by alkoxy of 1 to 12 carbon atoms.

3. A compound of formula I as set forth in claim 1, wherein $R^1$ and $R^2$ are chlorine, $R^3$ is 6-chlorine and A is $OCH_2CH=CH_2$.

4. A herbicidal composition comprising a carrier and a herbicidally effective amount of a 5-amino-1-phenyl-pyrazole-4-carboxylic acid derivative of the formula where $R^1$ is methyl, trifluoromethyl, chlorine or bromine, $R^2$ is chlorine, bromine, iodine or methylsulfonyl, $R^3$ is a methoxy radical in the 5-position or is hydrogen, chlorine or bromine, and A is $-OR^4$, where $R^4$ is alkenyl of 3 to 12 carbon atoms which is unsubstituted or substituted by phenyl, or is alkynyl of 3 to 10 carbon atoms, phenalkyl, where alkyl is of 1 to 8 carbon atoms, phenoxyalkyl, where alkyl is of 2 to 8 carbon atoms and the phenyl ring is unsubstituted or substituted by halogen, alkyl of 1 to 4 carbon atoms or methoxy, cycloalkylmethyl of 4 to 7 carbon atoms in total, or alkyl of 2 to 4 carbon atoms which is substituted by alkoxy of 1 to 12 carbon atoms, alkylthio of 1 to 12 carbon atoms, allyloxy, propargyloxy, chlorine or bromine, or a salt thereof.

5. A herbicidal composition as set forth in claim 4, and containing a 5-amino-1-phenyl-pyrazole-4-carboxylic acid derivative of the formula I wherein A is $-OR^4$, $R^4$ denoting alkenyl of 3 to 12 carbon atoms or alkyl of 2 to 4 carbon atoms which is substituted by alkoxy of 1 to 12 carbon atoms.

6. A method of combating the growth of unwanted plants which comprises applying to the plants or their location a herbicidally effective amount of a 5-amino-1-phenyl-pyrazole-4-carboxylic acid derivative of the formula I as set forth in claim 1, or a salt thereof.

* * * * *